United States Patent

Tabata et al.

[11] 4,328,381
[45] May 4, 1982

[54] ISOMERIZATION OF DICHLOROBUTENES

[75] Inventors: Itsuo Tabata; Seiichi Watanabe; Masayuki Shinoyama, all of Ohmi, Japan

[73] Assignee: Denki Kaguku Kogyo Kabushiki Kaisha, Tokyo, Japan

[21] Appl. No.: 212,124

[22] Filed: Dec. 2, 1980

[30] Foreign Application Priority Data

Dec. 25, 1979 [JP] Japan .................. 54/168547

[51] Int. Cl.$^3$ .............................................. C07C 17/24
[52] U.S. Cl. .................................................... 570/236
[58] Field of Search ........................................ 570/236

[56] References Cited

U.S. PATENT DOCUMENTS 3,751,493  8/1973  Ewell et al. ................... 570/236
3,927,130  12/1975  Kadowaki et al. ............. 570/236

FOREIGN PATENT DOCUMENTS 798889  7/1958  United Kingdom .
1296481  11/1972  United Kingdom .
1296482  11/1972  United Kingdom .
1296483  11/1972  United Kingdom .
1300430  12/1972  United Kingdom .
1315980  5/1973  United Kingdom .
1327983  8/1973  United Kingdom .

OTHER PUBLICATIONS

U.K. Search Report dated Feb. 24, 1981.

*Primary Examiner*—Delbert E. Gantz
*Assistant Examiner*—Joseph A. Boska
*Attorney, Agent, or Firm*—Oblon, Fisher, Spivak, McClelland & Maier

[57] ABSTRACT

An isomerization between 3,4-dichlorobutene-1 and 1,4-dichlorobutene-2 is carried out in the presence of a catalyst for isomerization as a combination of a copper compound and a dithiocarbamic acid derivative. The dithiocarbamic acid derivative is a compound having the formula

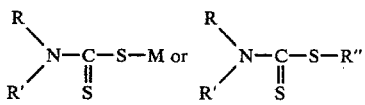

wherein R and R' are the same and different and respectively represent a $C_1$–$C_8$ alkyl group or an aryl group and M represents hydrogen atom or a metal atom or ammonium group and R" represents a $C_1$–$C_8$ alkyl group, an aryl group or a heterocyclic group such as mercaptobenzothiazole.

8 Claims, No Drawings

ISOMERIZATION OF DICHLOROBUTENES

BACKGROUND OF THE INVENTION

1. Field of the Invention

The present invention relates to an improved isomerization between 3,4-dichlorobutene-1 and 1,4-dichlorobutene-2.

2. Description of the Prior Arts

Heretofore, it has been proposed to heat a dichlorobutene in the presence of an isomerization catalyst of at least one of metal salts of copper, iron, zinc and aluminum.

However, these catalysts have relatively low catalytic activity. Accordingly, it has been proposed to improve the catalytic activity by adding various auxiliary catalysts to the metal salt. For example, an organic amine is added to a copper salt in British Pat. No. 798,889; an organic nitrile is added to cupric naphthenate in Japanese Unexamined Pat. No. 1514/1971; an organic dihydroxyl compound is added in Japanese Unexamined Pat. No. 11560/1972; and an aniline chlorinated derivative is added in Japanese Unexamined Pat. No. 18,808/1972.

As the catalyst for isomerization, it has been required to use a catalyst which has high catalytic activity and which causes less decomposition of dichlorobutene and less by-production of by-products having high boiling point and less corrosion of the apparatus.

The decomposition of dichlorobutene and the by-production of tar by-products having high boiling point cause not only a reduction of the yield of dichlorobutene but also a clogging of the apparatus to reduce the efficiency of the apparatus. When the amount of the catalyst increases, the catalytic activity is usually higher, however, it is preferable to be less amount of the catalyst in view of economy and recovery treatment of the wasted catalyst.

The catalyst having high catalytic activity usually attains the reaction at a low temperature whereby the decomposition of dichlorobutene and the production of tar high boiling by-product can be reduced. When the catalyst is used at a relatively high temperature, it is possible to decrease the amount of the catalyst whereby it is economically advantageous.

SUMMARY OF THE INVENTION

It is an object of the present invention to obtain the object dichlorobutene in high yield in an isomerization of dichlorobutenes in the presence of a catalyst having high catalytic activity at relatively low concentration of the catalyst to reduce the amount of the catalyst and to reduce corrosion of the parts of an apparatus contacting with the solution of the catalyst.

It is another object of the present invention to attain the reaction for the isomerization at relatively low temperature to reduce the decomposition of dichlorobutene and the by-production of tar by-products having high boiling point and to obtain the object dichlorobutene in high yield.

The foregoing and other objects of the present invention have been attained by providing an isomerization between 3,4-dichlorobutene-1 and 1,4-dichlorobutene-2 in the presence of a combination of a copper compound and a dithiocarbamic acid derivative, as a catalyst for isomerization.

DETAILED DESCRIPTION OF THE PREFERRED EMBODIMENTS

The copper compounds used as the catalyst for isomerization can be metallic copper and an organic or inorganic copper compounds preferably copper salts such as copper chloride, copper naphthenate and copper acetate, especially copper chloride and copper naphthenate.

The dithiocarbamic acid derivatives used as the catalyst for isomerization can be the compounds having the formula

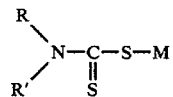

wherein R and R' are the same or different and respectively represent a $C_1$-$C_8$ alkyl group or aryl group; and M represents hydrogen atom or a metal atom preferably copper, iron, zinc, nickel, potassium or sodium atom or ammonium group; or the compounds having the formula

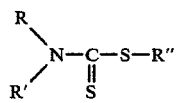

wherein R and R' are defined above and R" represents a $C_1$-$C_8$ alkyl group or an aryl group or a heterocyclic group such as mercaptobenzothiazol group.

The typical dithiocarbamic acid derivatives include dimethyldithiocarbamic acid, diethyldithiocarbamic acid, dipropyldithiocarbamic acid, dibutyldithiocarbamic acid and ethylphenyldithiocarbamic acid and salts thereof or esters thereof.

The dithiocarbamic acid derivatives also include diethylammonium dimethyldithiocarbamate, dimethylammonium dimethyldithiocarbamate, 2-benzothiazoyl diethyldithiocarbamate and methyl diethyldithiocarbamate. The typical dithiocarbamic acid derivatives include various metal salts such as copper, iron, zinc, nickel, potassium and sodium salts thereof and ammonium salts thereof.

The catalysts used in the present invention have high catalytic activity even though the concentration of the catalyst in dichlorobutene is low. The catalysts cause less production of tar or solid by-products and less corrosion of the apparatus.

The reaction temperature in the isomerization is usually in a range of 80° to 150° C. preferably 90° to 130° C.

When the reaction temperature is lower, the reaction velocity is lower whereas when the reaction temperature is higher, the decomposition of the dichlorobutene and the formation of the by-products having high boiling point are increased.

The concentration of the catalyst is depending upon the reaction temperature.

As the concentrations of the catalysts to the dichlorobutene, a concentration of the copper compound is usually in a range of 0.005 to 1 wt.%, especially 0.01 to 0.3 wt.% and a concentration of the dithiocarbamic acid derivative is usually in a range of 0.01 to 2 wt.% especially 0.05 to 1.5 wt.%. As the catalyst, it is possible to use two or more kinds of the copper compounds and two or more kinds of the dithiocarbamic acid derivatives.

The reaction pressure can be atmospheric pressure, higher or lower pressure.

The isomerization of the present invention can be carried out by a batch process or a continuous process using a distillation tower.

It is mostly preferable in an industrial operation to carry out the isomerization by adding the catalyst at the bottom of the distillation tower and discharging the object dichlorobutene as a distillate or a discharged product.

The distillation is preferably carried out under a reduced pressure of 40 to 760 Torr and the reaction is preferably carried out at the boiling point of the dichlorobutene.

If necessary, a reactor is equipped with the distillation tower to recycle the dichlorobutene from the reactor to the bottom of the tower.

In the continuous process, it is necessary to discharge a part of the reaction mixture at the bottom of the tower so as to prevent an accumulation of by-products having high boiling point. In this case, the catalyst is lost whereby it is preferable to add the catalyst so as to maintain a constant concentration of the catalyst.

The present invention will be further illustrated by certain examples.

EXAMPLES

In a 200 ml four necked flask equipped with a stirrer and a condenser, 150 g. of 1,4-dichlorobutene-2 was charged and heated under stirring it. The copper compound and one of the dithiocarbamic acid derivatives as a catalyst were simultaneously added to the dichlorobutene under controlling the reaction temperature at the specific temperature. After the addition of the catalyst, the mixture was stirred at the specific reaction temperature to react them. A part of the reaction mixture was sampled and analyzed by a gas chromatography. The reaction time was 30 minutes in the cases shown in Table 1 and 60 minutes in the cases shown in Table 3. The results are shown in Tables 1 and 3.

The content of 3,4-dichlorobutene-1 in 1,4-dichlorobutene-2 used as the starting materials in the examples was less than 0.5% by weight.

The content of copper in the cupric naphthenate was 5% by weight.

In Tables, 3,4-DCB designates 3,4-dichlorobutene-1; 1,4-DCB designates 1,4-dichlorobutene-2. The concentrations of the copper compound and the dithiocarbamic acid derivative shown by weight are based on the dichlorobutenes.

REFERENCES

In accordance with the process of the example except using each known catalyst for isomerization, each isomerization was carried out. The results of the references are shown in Tables 2 and 4. The reaction time was 30 minutes in the cases shown in Table 2. and 60 minutes in the cases shown in Table 4.

TABLE 1

Examples using cupric naphthenate:

| Exp. | Catalyst | Concentration of catalyst (wt. %) | Reaction temp. (°C.) |
|---|---|---|---|
| 1 | Cupric naphthenate | 0.40 | 130 |
| | Cu(II) dimethyldithiocarbamate | 0.05 | |
| 2 | Cupric naphthenate | 0.40 | 130 |
| | Zn dimethyldithiocarbamate | 0.05 | |
| 3 | Cupric naphthenate | 0.40 | 130 |
| | Na dimethyldithiocarbamate | 0.05 | |
| 4 | Cupric naphthenate | 0.40 | 130 |
| | Fe(III) dimethyldithiocarbamate | 0.05 | |
| 5 | Cupric naphthenate | 0.40 | 130 |
| | Zn ethylphenyldithiocarbamate | 0.05 | |
| 6 | Cupric naphthenate | 0.40 | 130 |
| | Zn di-n-butyldithiocarbamate | 0.05 | |
| 7 | Cupric naphthenate | 0.40 | 130 |
| | Zn diethyldithiocarbamate | 0.05 | |
| 8 | Cupric naphthenate | 0.40 | 130 |
| | Na diethyldithiocarbamate | 0.05 | |
| 9 | Cupric naphthenate | 0.40 | 130 |
| | Na di-n-butyldithiocarbamate | 0.05 | |
| 10 | Cupric naphthenate | 0.40 | 130 |
| | N,N-diethyldithiocarbamoyl-2-mercaptobenzothiazole | 0.05 | |

| Exp. | Composition (wt. %) | | |
|---|---|---|---|
| | 3,4-DCB | cis-1,4-DCB | trans-1,4-DCB |
| 1 | 22.99 | 6.75 | 70.26 |
| 2 | 25.44 | 7.07 | 67.49 |
| 3 | 21.72 | 6.84 | 71.44 |
| 4 | 22.16 | 6.83 | 71.01 |
| 5 | 23.71 | 6.88 | 69.41 |
| 6 | 23.06 | 6.84 | 70.10 |
| 7 | 24.49 | 6.93 | 68.58 |
| 8 | 21.51 | 6.34 | 72.15 |
| 9 | 21.12 | 5.83 | 73.05 |
| 10 | 21.59 | 5.80 | 72.61 |

TABLE 2

References using cupric naphthenate:

| Exp. | Catalyst | Concentration of catalyst (wt. %) | Reaction temp. (°C.) |
|---|---|---|---|
| 1 | Cupric naphthenate | 0.40 | 130 |
| | triphenylphosphine oxide | 0.05 | |
| 2 | Cupric naphthenate | 0.40 | 130 |
| | methylurea | 0.05 | |
| 3 | Cupric naphthenate | 0.40 | 130 |
| | acetoxime | 0.05 | |
| 4 | Cupric naphthenate | 0.40 | 130 |
| | 1,4-dicyanobutene-2 | 0.05 | |
| 5 | Cupric naphthenate | 0.40 | 130 |
| | glutaronitrile | 0.05 | |
| 6 | Cupric naphthenate | 0.40 | 130 |
| | p-nitroaniline | 0.05 | |
| 7 | Cupric naphthenate | 0.40 | 130 |
| | nitrobenzene | 0.05 | |
| 8 | Cupric naphthenate | 0.40 | 130 |
| | propane-1,3-diol | 0.05 | |
| 9 | Cupric naphthenate | 0.40 | 130 |
| | dibenzylsulfide | 0.05 | |
| 10 | Cupric naphthenate | 0.40 | 130 |
| | methylphenylsulfide | 0.05 | |
| 11 | Cupric naphthenate | 0.40 | 130 |
| | methyl-p-tolysulfide | 0.05 | |

| Exp. | Composition (wt. %) | | |
|---|---|---|---|
| | 3,4-DCB | cis-1,4-DCB | trans-1,4-DCB |
| 1 | 19.61 | 6.75 | 73.64 |
| 2 | 16.68 | 6.91 | 76.41 |
| 3 | 13.58 | 7.56 | 78.86 |
| 4 | 17.63 | 7.37 | 75.00 |
| 5 | 17.39 | 7.35 | 75.26 |
| 6 | 20.07 | 6.76 | 73.17 |
| 7 | 20.19 | 6.73 | 73.08 |
| 8 | 18.70 | 7.34 | 73.96 |
| 9 | 14.44 | 4.95 | 80.61 |
| 10 | 14.31 | 4.96 | 80.73 |
| 11 | 13.59 | 4.95 | 81.46 |

TABLE 3

| Examples using cuprous chloride: | | | |
|---|---|---|---|
| Exp. | Catalyst | Concentration of catalyst (wt. %) | Reaction temp. (°C.) |
| 1 | CuCl | 0.046 | 130 |
|   | Cu(II) dimethyldithiocarbamate | 0.033 | |
| 2 | CuCl | 0.046 | 130 |
|   | Zn dimethyldithiocarbamate | 0.046 | |
| 3 | CuCl | 0.046 | 130 |
|   | Zn ethylphenyldithiocarbamate | 0.075 | |
| 4 | CuCl | 0.046 | 130 |
|   | Zn di-n-butyldithiocarbamate | 0.075 | |
| 5 | CuCl | 0.046 | 130 |
|   | Zn diethyldithiocarbamate | 0.075 | |
| 6 | CuCl | 0.046 | 130 |
|   | Na di-n-butyldithiocarbamate | 0.075 | |
| 7 | CuCl | 0.249 | 100 |
|   | Zn ethylphenyldithiocarbamate | 0.80 | |

| | Composition (wt %) | | |
|---|---|---|---|
| Exp. | 3,4-DCB | cis-1,4-DCB | trans-1,4-DCB |
| 1 | 22.48 | 5.21 | 72.31 |
| 2 | 22.11 | 5.30 | 72.59 |
| 3 | 25.89 | 5.96 | 68.15 |
| 4 | 25.99 | 5.90 | 68.11 |
| 5 | 24.90 | 5.64 | 69.46 |
| 6 | 21.56 | 5.39 | 73.05 |
| 7 | 22.67 | 5.76 | 71.57 |

TABLE 4

| References using cuprous chloride: | | | |
|---|---|---|---|
| Exp. | Catalyst | Concentration of catalyst (wt. %) | Reaction temp. (°C.) |
| 1 | CuCl | 0.046 | 130 |
|   | triphenylphosphine oxide | 0.075 | |
| 2 | CuCl | 0.046 | 130 |
|   | acetoxine | 0.075 | |
| 3 | CuCl | 0.046 | 130 |
|   | triethanolamine | 0.075 | |
| 4 | CuCl | 0.046 | 130 |
|   | methylurea | 0.075 | |
| 5 | CuCl | 0.046 | 130 |
|   | Dibenzylsulfide | 0.075 | |
| 6 | CuCl | 0.046 | 130 |
|   | methylphenylsulfide | 0.075 | |
| 7 | CuCl | 0.046 | 130 |
|   | methyl p-tolylsulfide | 0.075 | |
| 8 | CuCl | 0.046 | 130 |
|   | parachloroaniline | 0.075 | |

| | Composition (wt. %) | | |
|---|---|---|---|
| Exp. | 3,4-DCB | cis-1,4-DCB | trans-1,4-DCB |
| 1 | 18.88 | 5.02 | 76.10 |
| 2 | 14.26 | 5.05 | 80.69 |
| 3 | 12.45 | 5.14 | 82.41 |
| 4 | 11.62 | 5.08 | 83.30 |
| 5 | 18.62 | 5.00 | 76.38 |
| 6 | 19.23 | 5.04 | 75.73 |
| 7 | 19.56 | 5.04 | 75.40 |
| 8 | 13.74 | 5.00 | 81.26 |

We claim:

1. In an isomerization between 3,4-dichlorobutene-1 and 1,4-dichlorobutene-2 in the presence of a catalyst, an improvement characterized in that the catalyst for isomerization is a combination of a copper compound and a dithiocarbamic acid derivative.

2. The isomerization according to claim 1 wherein said dithiocarbamic acid derivative is a compound having the formula

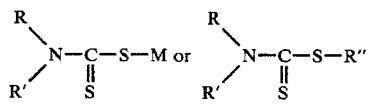

wherein R and R' are the same and different and respectively represent a $C_1$–$C_8$ alkyl group or an aryl group and M represents hydrogen atom or a metal atom or ammonium group and R" represents a $C_1$–$C_8$ alkyl group, an aryl group or a heterocyclic group such as mercaptobenzothiazole.

3. The isomerization according to claim 1 wherein said copper compound is a metallic copper, copper chloride, copper naphthenate or copper acetate.

4. The isomerization according to claim 1 wherein said isomerization is carried out at a temperature ranging from 80° to 150° C.

5. The isomerization according to claim 1 wherein a concentration of said copper compound is in a range of 0.005 to 1% by weight and a concentration of said dithiocarbamic acid derivative is in a range of 0.01 to 2% by weight.

6. The isomerization according to claim 1 wherein said catalyst is placed at the bottom of a distillation tower and the reaction is performed at the boiling point of dichlorobutene to distil off the object product.

7. The isomerization according to claim 1 wherein dichlorobutene is recycled between a reactor and a bottom of a distillation tower.

8. The isomerization according to claim 1 wherein 1,4-dichlorobutene-2 is isomerized into 3,4-dichlorobutene-1.

* * * * *

UNITED STATES PATENT AND TRADEMARK OFFICE
CERTIFICATE OF CORRECTION

PATENT NO. : 4,328,381
DATED : May 4, 1982
INVENTOR(S) : Itsuo, Tabata et. al.

It is certified that error appears in the above—identified patent and that said Letters Patent is hereby corrected as shown below:

On the title page Assignee should read:

[73] -- Assignee: DENKI KAGAKU KOGYO KABUSHIKI KAISHA, Tokyo, Japan --

Signed and Sealed this

Twenty-second Day of June 1982

[SEAL]

Attest:

Attesting Officer

GERALD J. MOSSINGHOFF

Commissioner of Patents and Trademarks